US011730456B2

(12) United States Patent
Martinez Hurtado (10) Patent No.: US 11,730,456 B2
(45) Date of Patent: Aug. 22, 2023

(54) METHOD AND DEVICE FOR ESTIMATION OF OVULATION DATE

(71) Applicant: Colorimetrix GmbH, Munich (DE)

(72) Inventor: Juan Leonardo Martinez Hurtado, Munich (DE)

(73) Assignee: COLORIMETRIX GmbH, Munich (DE)

( * ) Notice: Subject to any disclaimer, the term of this patent is extended or adjusted under 35 U.S.C. 154(b) by 1107 days.

(21) Appl. No.: 16/468,391

(22) PCT Filed: Dec. 13, 2017

(86) PCT No.: PCT/EP2017/082664
§ 371 (c)(1),
(2) Date: Jun. 11, 2019

(87) PCT Pub. No.: WO2018/109025
PCT Pub. Date: Jun. 21, 2018

(65) Prior Publication Data
US 2019/0307432 A1 Oct. 10, 2019

(30) Foreign Application Priority Data

Dec. 13, 2016 (EP) .................................... 16203855

(51) Int. Cl.
*G01N 33/76* (2006.01)
*G01N 33/543* (2006.01)
*A61B 10/00* (2006.01)

(52) U.S. Cl.
CPC ... *A61B 10/0012* (2013.01); *G01N 33/54388* (2021.08); *G01N 33/76* (2013.01); *A61B 10/007* (2013.01); *G01N 2333/59* (2013.01)

(58) Field of Classification Search
CPC .............. A61B 10/0012; A61B 10/007; G01N 33/558; G01N 33/76; G01N 2333/59
See application file for complete search history.

(56) References Cited

U.S. PATENT DOCUMENTS 3,986,494 A   10/1976   Preti et al.
4,010,738 A    3/1977   Preti et al.
(Continued)

FOREIGN PATENT DOCUMENTS

CN        1575778 A     2/2005
CN      101785686 B     8/2012
(Continued)

OTHER PUBLICATIONS

International Search Report and Written Opinion dated Jun. 27, 2019 in corresponding International Patent Application No. PCT/EP2017/082664, 8 pages.
(Continued)

*Primary Examiner* — Changhwa J Cheu
(74) *Attorney, Agent, or Firm* — Buchanan Ingersoll & Rooney PC (57) ABSTRACT

According to a first aspect of the invention, there is provided a device for estimation of an ovulation date, comprising a camera, configured to obtain colour data of successive FSH test strips and a processor, configured to evaluate the colour data obtained by the camera. The processor is configured to determine a concentration value of each successive FSH test strip based on the data of the camera and to output a signal, if the processor determines that a first FSH downward trend of the FSH test strip values is occurring in the successive FSH test strips.

16 Claims, 6 Drawing Sheets

(56) References Cited

U.S. PATENT DOCUMENTS

| | | | |
|---|---|---|---|
| 6,352,862 | B1 | 3/2002 | Davis et al. |
| 8,374,989 | B2 | 2/2013 | Lee et al. |
| 8,496,597 | B2 | 7/2013 | James et al. |
| 9,097,665 | B2 * | 8/2015 | Wang .................. G01N 21/55 |
| 9,155,522 | B2 | 10/2015 | James et al. |
| 9,155,523 | B2 | 10/2015 | James et al. |
| 9,206,254 | B2 | 12/2015 | Decourtye et al. |
| 2003/0119202 | A1 * | 6/2003 | Kaylor ................ G01N 33/558 |
| | | | 436/514 |
| 2004/0253142 | A1 | 12/2004 | Brewster et al. |
| 2005/0010128 | A1 | 1/2005 | Shiraishi et al. |
| 2006/0005234 | A1 | 1/2006 | Birk et al. |
| 2009/0326410 | A1 | 2/2009 | Bittner |
| 2010/0191696 | A1 | 7/2010 | Lee et al. |
| 2013/0065321 | A1 | 3/2013 | Nazareth et al. |
| 2013/0296735 | A1 | 11/2013 | James et al. |
| 2014/0134649 | A1 | 5/2014 | Decourtye et al. |
| 2015/0094227 | A1 | 4/2015 | McCarthy et al. |
| 2015/0359458 | A1 | 12/2015 | Erickson et al. |
| 2016/0030011 | A1 | 2/2016 | James et al. |
| 2016/0066894 | A1 | 3/2016 | Barton-Sweeney |
| 2016/0139156 | A1 | 5/2016 | Lakdawala |
| 2016/0196383 | A1 | 7/2016 | Wang et al. |
| 2018/0149600 | A1 * | 5/2018 | Farrell ............. G01N 33/48785 |
| 2018/0271500 | A1 | 9/2018 | James et al. |
| 2019/0307432 | A1 | 10/2019 | Martinez Hurtado |

FOREIGN PATENT DOCUMENTS

| | | |
|---|---|---|
| CN | 101528138 B | 1/2013 |
| CN | 105765388 A | 4/2018 |
| EP | 0291194 A1 | 11/1988 |
| EP | 3554386 A1 | 10/2019 |
| WO | 2016142610 A1 | 9/2016 |
| WO | 2018109025 A1 | 6/2018 |

OTHER PUBLICATIONS

Petra Frank-Herrmmann, C Gnoth, S Baur, T Strowitzki & G Freundi, "Determination of the fertile window: Reproductive competence of women—European cycle database", Gynecological Endocrinology, Jun. 2005, 20(6) p. 305-312.
International Search Report and Written Opinion dated Feb. 20, 2018 in corresponding European Patent Application No. 16 203 855.8, 14 pages.
Communication Under Article 94(3) EPC dated Jul. 29, 2020 in corresponding European Patent Application No. 17 811 338.7-1122 (5 pages).
Communication Under Article 94(3) EPC dated Dec. 14, 2020 in corresponding European Patent Application No. 17 811 338.7-1122 (4 pages).
Chinese Office Action dated May 8, 2021 in corresponding Chinese Patent Application No. 201780076978.8 (9 pages).
Canadian Office Action dated May 21, 2020 in corresponding Canadian Patent Application No. 3,043,270 (4 pages).
Canadian Office Action dated Apr. 20, 2021 in corresponding Canadian Patent Application No. 3,043,270 (4 pages).
Canadian Office Action dated Sep. 22, 2022 in corresponding Canadian Patent Application No. 3,043,270 (4 pages).

* cited by examiner

METHOD AND DEVICE FOR ESTIMATION OF OVULATION DATE

CROSS-REFERENCE TO RELATED APPLICATIONS

This patent application is the U.S. national stage application under 35 U.S.C. § 371 for International Patent Application No. PCT/EP2017/082664, filed on Dec. 13, 2017, which claims the benefit of priority to European Patent Application No. 16 203 855.5, filed on Dec. 13, 2016, the entire contents of each is incorporated herein by reference.

FIELD OF THE INVENTION

The present invention relates to a device for reading and interpreting FSH test strips for the estimation of an ovulation date, comprising a camera, configured to obtain colour data of successive test strips and a processor, configured to evaluate the colour data obtained by the camera. The present invention also relates to a method for estimation of an ovulation date.

BACKGROUND

It is known to use test strips to estimate an ovulation date of a woman. Exemplary test strips are disclosed in EP 0 291 194 B2, U.S. Pat. No. 9,206,254 B2 and WO 2016 142 610 A1. Luteinizing hormone (LH) test strips have traditionally been used to estimate an ovulation date of a woman, wherein the urine comprises LH to be detected. These test strips are configured such that a urine sample is provided at one end of the test strip. The urine, together with the analyte LH, permeates through the strip material. The sample progresses into a detection zone in the test strip. In the detection zone, a specific binding reagent for the suspected analyte is mobilized. The analyte, which is present in the urine sample, can therefore become bound within the detection zone. The amount of analyte, which is bound in the detection zone, can then be optically observed by labelling reagents. Typical test strips also comprise a control zone to convey an unrelated signal to the user that the device has worked.

Such test strips can be analysed in devices such as disclosed in US 2004/0253142 A1, US 2013/0065321 A1 or U.S. Pat. No. 6,352,862 B1. In these devices, the user can directly view at the detection zone and the control zone of the test strip. Alternatively, devices could be provided to illuminate the detection zone of the test strip by light sources with nearly monochromatic light and determine if the intensity in the detection zone has reached a certain threshold. In this case, the device may be configured to output a respective positive or negative signal.

These devices utilize the characteristics of hormonal levels before the ovulation date. In more detail, the LH level has a sharp rise about 24 to 48 hours before the ovulation date. This feature is also referred to as LH surge. The LH peak occurs around 6 to 28 hours with an average of around 17 hours before the ovulation date. This means the ovulation has a probability distribution centred at that time. By monitoring the LH level daily around the time ovulation may be expected, the LH peak can be detected. Ovulation happens after the LH peak. As a consequence, the chances of pregnancy can be determined in the associated fertile window. In this regard, the fertile window is described, for example, in "*Reproductive competence of women—European cycle databases*", Petra Frank-Herrmann, C Gnoth, S Baur, T Strowitzki & G Freundl, *Gynecological Endocrinology*, June 2005; 20(6): 305-312". The fertile window precedes ovulation and spans one day after ovulation. It lasts 9 to 11 days and has a distinctive Gaussian probability distribution with higher probabilities of pregnancy two, three and four days before ovulation.

Further hormones such as the follicle-stimulating hormone (FSH) also show a characteristic rise before the ovulation date. The FSH level rises about 24 to 48 hours before the ovulation date. This feature is also referred to as FSH surge. The FSH peak occurs around 2 to 19 hours with an average of around 12 hours before the ovulation date. Since the amplitude of the LH rise and subsequent LH peak is usually higher than the FSH rise/peak, LH is typically used for estimating the ovulation date.

There are strong correlations between serum concentrations and urine concentration values of the ovulation related hormones. These hormones are conventionally monitored in first morning urine to estimate the ovulation date. Typically, lateral flow immunoassays (LFIA) test strips for these hormones, also known as ovulation prediction kits, are used. Monitoring the LH or FSH rise occurring just before the ovulation enables an estimation of the ovulation date. However, monitoring the LH or FSH rise occurring before the ovulation only enables the estimation of the ovulation date about 24 to 48 hours before ovulation. Similarly, estrogen or progesterone test strips are used to estimate ovulation dates. Estrogen rises 2 to 4 days before ovulation with a peak value at the ovulation date, whereas progesterone rises after ovulation has occurred with a broad peak value 7 days post ovulation.

The date estimation accuracy of these known methods is limited, so that a reliable estimation of the ovulation date can only be obtained around two days before the actual ovulation happens.

It would be desirable to have a device for estimating the ovulation date and a respective method, which is more accurate than the current devices, and which are able to estimate the ovulation date a longer period in advance.

SUMMARY

According to a first aspect of the invention, there is provided a device for estimation of an ovulation date, comprising a camera, configured to obtain colour data of successive daily FSH test strips and a processor, configured to evaluate the colour data obtained by the camera. The processor is configured to evaluate a concentration value for each successive test strip based on the colour data of the camera and to output a signal, if a first FSH downward trend is determined by the processor from the beginning of a menstrual cycle.

The camera may comprise a CMOS sensor or a CCD sensor able to sense photons from the electromagnetic spectrum, or colours of test strips. The processor performs an analysis of the colouration by processing the colour information from the colour space (RGB, sRGB, HUV, LAB), then transforming this information mathematically, for example, but not limited to, matrix multiplication, rotation, transposition normalization, etc., resulting in rotation, scaling and skewing of the values, to fulfil standard colour spaces notation, or to non-conventional colour spaces resulting from said mathematical transformations. The transformation may include a step for fixing the standard illuminant or adjusting the standard illuminant of said resulting colour space. The transformation may result in a colour space on which a colouration or set of colourations are represented as a larger fraction of the resulting colour space. The analysis of the colouration of test strips by the processor is used to assign hormonal concentration values to the colours detected by the camera. Then, a set of colour values in the defined colour space (for example R,G,B) is assigned a concentration value. In this way, concentration values are mapped to the analysed colour space, thus leading to a high level of accuracy regarding different hormonal concentration values.

According to the present invention, a pre-calibration step may be performed by the processor prior to reporting hormonal values. In this calibration step, the processor obtains colour data from a set of test strips exposed to standard concentration values before an ovulation estimation measurement cycle. At least two concentration values can be used as minimum, for example one that generates no change in colouration of the test zone of the strip, and one that generates the maximum change in colouration of said test zone. Preferably, a minimum of five concentration values is used. In order to decrease the concentration difference between the calibrated values and increase the accuracy of the measurement, the processor may be calibrated by using as many test strips as possible exposed to as many standard concentrations within the exposure range of the test strip.

The term "concentration value" also encompasses percentage values, or mathematical transformations of said values to any other numerical values, which mapped onto the colour space may comprise further transformations, for example but not limited to logarithmic series, power series, prime series, or arbitrary number series for which one real concentration value corresponds to one mapped numerical value.

According to the present invention, colouration and not intensity is measured by the device. Measuring colouration of the test strips allows for the measurement to be performed under normal ambient conditions, for example, but not limited to, incandescent light, florescent light, day light, LED light, candle light, etc. The intensity of the light source under which the device performs a measurement can be expressed in terms of illuminance ranging from, but not limited to 41 lux to 41000 lux.

The device then measures hormonal test strip values from strips exposed to urine containing hormones at different concentration values. The colour information from the test strips is mapped to the colour space as described above, and associated to a corresponding concentration from the calibration with standard concentrations. Then, the processor interprets the mapped colour and associated concentrations to determine the hormonal values of the test strips.

The device then measures hormonal values overtime and stores them via the processor. The values are collected from the FSH strip or from multiple FSH strips at time intervals, for example but not limited to, daily measurements. These daily measurements are collected for example, but not limited to, first morning urine. There is an excellent correlation from urine values to serum values from the hormones involved in ovulation. The processor then builds a measurement profile associated with the menstrual cycle, for example, but not limited to, the first day of a menstrual cycle.

The hormonal first FSH downward trend to be observed after multiple measurements indicate a probability distribution of an ovulation date of a woman many days in advance of the actual ovulation, and well before an LH peak, a high FSH peak, or a progesterone rise or peak can be observed. The processor then determines that a first downward trend of the FSH values is occurring in the successive FSH test strip measurements. By evaluating a change in the form of a first downward trend in the FSH level contained in successive test samples, the actual ovulation date can be estimated as far as five to seven days with an average of six days in advance. In more detail, further to the rise of the FSH level about 24 to 48 hours before the ovulation as described above, the FSH level rises to a comparably shallow peak between the beginning of the cycle and the ovulation date. The FSH level then decreases to a depression before raising again to the characteristic peak at 24 to 48 h before ovulation. The peak amplitude of this first peak is typically less than the peak amplitude of the second peak which occurs about 24 to 48 hours before the ovulation. The first FSH shallow peak occurs from 12 to 22 days before ovulation, this variability implies that the duration of the shallow peak from cycle to cycle and women to women is different and variable. However, if the FSH values are monitored well in advance of the ovulation date, the first shallow peak may be observed and the following first downward trend detected. This first downward trend indicates that the first FSH shallow peak occurred and can thus be used to estimate the ovulation date well in advance of the conventionally possible 24 to 48 hours before the ovulation.

The measurement of the first downward trend of FSH may be calculated by taking into account for example, but not limited to, six values, which can be continuous or discontinuous, preferably continuous. Preferably, these six values correspond to six test strip measurements of six consecutive days. Mathematical and statistical analysis of those values is performed to qualify them as the first downward trend of FSH. For example, but not limited to, numerical regressions, linear, polynomial, logarithmic, exponential; or derivatives, curve fitting, integration, or any other suitable mathematical and statistical analysis. These mathematical calculations can be applied to said consecutive values to achieve an ovulation date prediction with high accuracy. A smaller subset of those values may also be utilized and compared with previous or subsequent groups of values within the set or overlapping with different measurements in order to predict ovulation well in advance.

Particularly, to achieve the highest accuracy in prediction of an ovulation date, a set of six consecutive FSH values is analyzed. The six FSH values are obtained by daily measurements. This set of values is analyzed by determining the slope of the linear regression of the six values. Additionally, the slope of the linear regression of the first five values and the slope of the linear regression of the last five values within the set of six values are determined. Thus, three slopes are determined in total. The three slopes are compared amongst themselves and it is determined, if the three slopes fall within a predetermined range. In addition, the correlation coefficient of the three linear regressions is also compared.

The correlation coefficient is applied to the hormonal measurements over time and it is, for example but not limited to, the product-moment correlation coefficient or the Pearson correlation coefficient. This coefficient is the covariance of the days and hormonal values divided by the product of their standard deviations.

A significant downward trend may be determined if the slope of the linear regression of the subset of the first five values is lower than the slope of the linear regression of the subset of the last five values. As an additional criterion, the respective slopes of the linear regression of the set of six values and the two subsets of five values must be negative.

A further comparison to increase accuracy would include the correlation coefficients to be within a range. For example, the coefficients and the slopes should be negative.

In a particular example, the slope of the first five values is smaller than 0 and the slope of the last five values is smaller than −0.1, and the correlation coefficients of said slopes are −0.07 and −0.12 respectively. In another example, the derivative of the set of six values and of the subsets of the first five and last five values is calculated numerically by central differences, and also added to the comparison.

FSH hormonal data obtained by the device may include test strip variability noise, or instrument noise, or ambient conditions variability noise. Noise reduction algorithms may be utilized to enhance the quality of data.

The device may further comprise a display, configured to display the estimation results of the device. The user may be instructed on the display how to position the camera to obtain the colour data of the test strip. Thus, the user may obtain colour data of test strips with immediate feedback whether the colour data suffices the requirements of the device. Also, the results of the estimation may be displayed to the user immediately.

The used test strips may be conventional known FSH test strips, or multi-analyte test strips responding to one or multiple analytes. A user may use multiple test strips such as LH and/or progesterone test strips together with the FSH test strips to monitor the corresponding hormones with the device according to the invention. The user may also use FSH test strips exclusively to monitor and determine the first FSH downward trend. The user may also use subsequent LH and/or Progesterone test strips exclusively to confirm the ovulation date after the first FSH downward trend has been detected. The user may also use LH and/or Progesterone tests strips exclusively in subsequent menstrual cycles after the first cycle where the first FSH downward trend is detected to confirm the ovulation dates. Multi-analyte test strips may be utilized to monitor multiple hormones in addition to FSH with a single test strip for each measurement.

The test strips may each comprise a blank zone onto which no test samples are attached to, a detection zone, and a control zone, and wherein the processor may be configured to calibrate the device based on the obtained camera data of these zones. The test strips may comprise multiple detection zones, multiple blank zones, and multiple control zones, wherein the processor may be configured to evaluate the camera data of these zones. The detection, control, and blank zones may vary in colour or have the same colour. The device may analyze these colors together or separately as described above.

In more detail, the control zone is a zone onto which the applied test sample permeates and which gives a clear indication whether the application of the test sample was successful. The blank zone is typically a white portion of the test strip which acquires a background colouration that may differ to its original colour after exposure to the testing fluid. The test zone is a zone onto which a colouration change is observed depending on the concentration value of the analytes in the test 'problem' sample. Typically a maximum concentration value associated with the sensitivity of the test strip corresponds in colouration to the control zone.

The device utilizes the colouration of the test zone to be mapped to concentrations from the standard calibration described above, and report a concentration. Furthermore, the colour mapping to concentration can also be applied to the control zone and blank zone and the device may utilize the control zone and the blank zone to perform a local calibration on which the colour information is utilized to evaluate the quality of the test strip, the correct usage of the test strip, or the illuminating conditions. Furthermore, the mapping of colouration can also be utilized onto any area of the test strip to identify the type of hormonal test strip used.

In a similar configuration, the device may utilize the control zone and the blank zone to perform the standard concentration calibration as described above on which known concentrations are associated to the colouration of the blank and control zones. For calibration, the colour data of this control zone, i.e. the colour of the control zone, is set to a maximum hormonal level. Furthermore, colour data of the blank zone onto which no test samples are applied, i.e. the colour of this zone, is set to a minimum hormonal level. The reliability is increased due to the independence of the measurement from the illumination of the test strip.

The processor may be configured to calibrate the device based upon at least one previous measurement cycle of the device.

In this regard, the device may be employed on successive menstruation cycles, corresponding to successive measurement cycles of the device. The fertile window of each woman may be different within a menstruation cycle. If the fertile window within a menstruation cycle is unknown, it may be necessary to start with evaluating test strips from day one of the menstruation cycle. Successive measurement cycles of the device may be performed with a close tracking of the fertile window with less test strip evaluations needed. In more detail, the device may track the ovulation date with respect to the end of the menstruation and/or with respect to the start of the daily measurement. For successive measurement cycles, the device may instruct the user when to start with the measurement after menstruation.

Also, the hormonal levels of each woman and each cycle differ. By evaluating the absolute hormonal levels of previous measurement cycles, the base hormonal levels of the woman may be estimated. Also, peaks of the hormonal levels may be estimated. Furthermore, the hormonal levels of a first FSH downward trend may be estimated on basis of previous measurement cycles. Depending on the estimated hormonal levels, a first downward trend of FSH may be determined with higher accuracy. The device detects and predicts ovulation based on hormonal levels from each individual cycle and only uses pervious cycle information to better position the downward trend analysis.

The device may be configured as a smartphone. The display, the camera and the processor may be any known conventional display, camera and processor. The processor may be part of electric circuitry. The electric circuitry may be part of a controller. The controller may control the display and/or the camera. The display, the camera and the processor may be provided in the smartphone housing. The camera and the display may be provided in the smartphone housing in contact with the outside of the smartphone while the processor may be encapsulated in the smartphone housing.

Smartphones comprise cameras, processors, sensors and displays. Furthermore, smartphones are widely used today and carried by most people on a daily basis. By using a smartphone, the accuracy of high quality cameras for evaluation of the test strips may be utilized. Also, there is no need to provide an additional analyzation device. Smartphones also comprise a power supply such as a battery.

The device may use multiple connectivity, for example wifi, bluetooth, LTE, 3G, 4G, 5G to send and transmit data obtained or generated by the device elsewhere. Data may include results of the calculations or any other data associated with the usage of the device, for example but not limited to, personal information, menstrual cycle information, location, time, and any other information provided by the device internal sensors or by user input.

The camera may be configured to also obtain, and the processor to evaluate, colour data of other test strips, for example LH test strips, strips for determination of estrogen (E) and/or strips for determination of progesterone (PG) or any other lateral flow immunoassay test strip (LFIAs) The camera may be configured to analyze multi-analyte test strips combining two or more analytes in one test strip.

The ovulation estimation may be accompanied by a confirmation of the ovulation date by measuring LH by similar means and determining its rise or peak value or downward trend. As described above, the LH level has a sharp rise about 24 to 48 hours before the ovulation date. The robustness of the ovulation estimation may thus be enhanced by additionally tracking LH levels with LH test strips. In more detail, the system estimates the ovulation date five to six days in advance by means of the first FSH downward trend. After that and preferably also before that estimation, the LH values are monitored. About two days before the ovulation date, the estimated ovulation date can be confirmed by monitoring the comparable steep rise of the LH level, the LH peak or the LH downward trend The calculation of these rise, peak or downward trends of LH may be performed by analyzing LH measurements of the device and applying mathematical and statistical analysis by similar means as described above for FSH.

For such a confirmation of the ovulation, the processor may be configured to output a further second signal, if the processor determines that a rise or peak or first downward trend of the LH value is occurring in successive LH test strips.

This confirmation may be accompanied by an additional confirmation by means of measuring test strips for progesterone hormonal levels. The progesterone hormonal levels rise after ovulation and may be used as a confirmation of the release of the ovule. For measuring of progesterone, pregnanediol, a metabolized product of progesterone in urine, may be detected and monitored by similar means, i.e. camera and strips, as disclosed above with respect to FSH and LH. The ovulation is further confirmed if the processor determines a rise, peak, or downward trend in the progesterone level after the ovulation. Similarly, the trend is calculated on successive measurements of progesterone by the processor to identify an upward trend, downward trend or peak, as described above for FSH.

The processor may be configured to output a further third signal, if the processor determines that a rise or peak or first downward trend of the progesterone value is occurring in successive progesterone test strips after the rise or peak or first downward trend of the LH value in the LH test strips is determined.

The second and/or the third signals are confirmation signals confirming an ovulation. The user may therefore be aware of an upcoming ovulation five to seven days in advance and may also be provided with a confirmation as the ovulation date approaches. After the ovulation, the user may check if the ovulation actually happened, thereby tracking the whole fertile window with high accuracy. Also, the user may check if any medical issue is present or if the ovulation cycle is within normal behavior. The device may output a respective further signal to the user, indicating whether or not any medical issue may exist by comparing hormonal profiles with normal expected values.

The processor may be configured to output further signals from multiple LFIA strips for which the device performs measurements and mathematical analysis by the means described above.

The processor may be configured to compare signals from multiple LFIA strips with themselves or with other LFIA strip measurements to increase the accuracy of the determination of the ovulation date. Such comparisons include, for example but not limited to, analysis of variance, co-variance, standard deviations, linear regression, logistic regression, Naive Bayes, means, nearest neighbors, principal component analysis and other machine learning algorithms. The device may compare for example the time differences between the measured FSH downward trend and the LH peak values and the PG rise.

According to a second aspect of the invention, there is provided a method for estimation of an ovulation date, wherein the method comprises the steps of applying successive test samples comprising an analyte on successive FSH test strips. A camera obtains colour data of the FSH test strips. A processor evaluates the colour data obtained by the camera. The processor determines a concentration value of each successive FSH test strip based on the data of the camera and outputs a signal, if the processor determines that a first FSH downward trend of the FSH test strip values is occurring in the successive FSH test strips.

Preferably, a wider colour spectrum is obtained by the camera than by using conventional nearly monochromatic light sources and corresponding light receiving elements. Since the colour—indicating the amount of analyte in the detection zone—varies over the colour spectrum, using a wider colour spectrum enables that small changes in the amount of analyte present in the detection zone can be determined more accurately than just a threshold intensity. Thus, the concentration values in the sample to which the test strips are exposed can be determined more accurately, and therefore, a hormonal profile can be built using the device. Having a hormonal profile allows for the mathematical and statistical analysis to be applied to the collection of measured values, and thus the first downward trend of FSH can be detected many days in advance of the actual ovulation date.

BRIEF DESCRIPTION OF THE DRAWINGS

The invention will be further described, by way of example only, with reference to the accompanying drawings in which.

DETAILED DESCRIPTION

Figure 1:
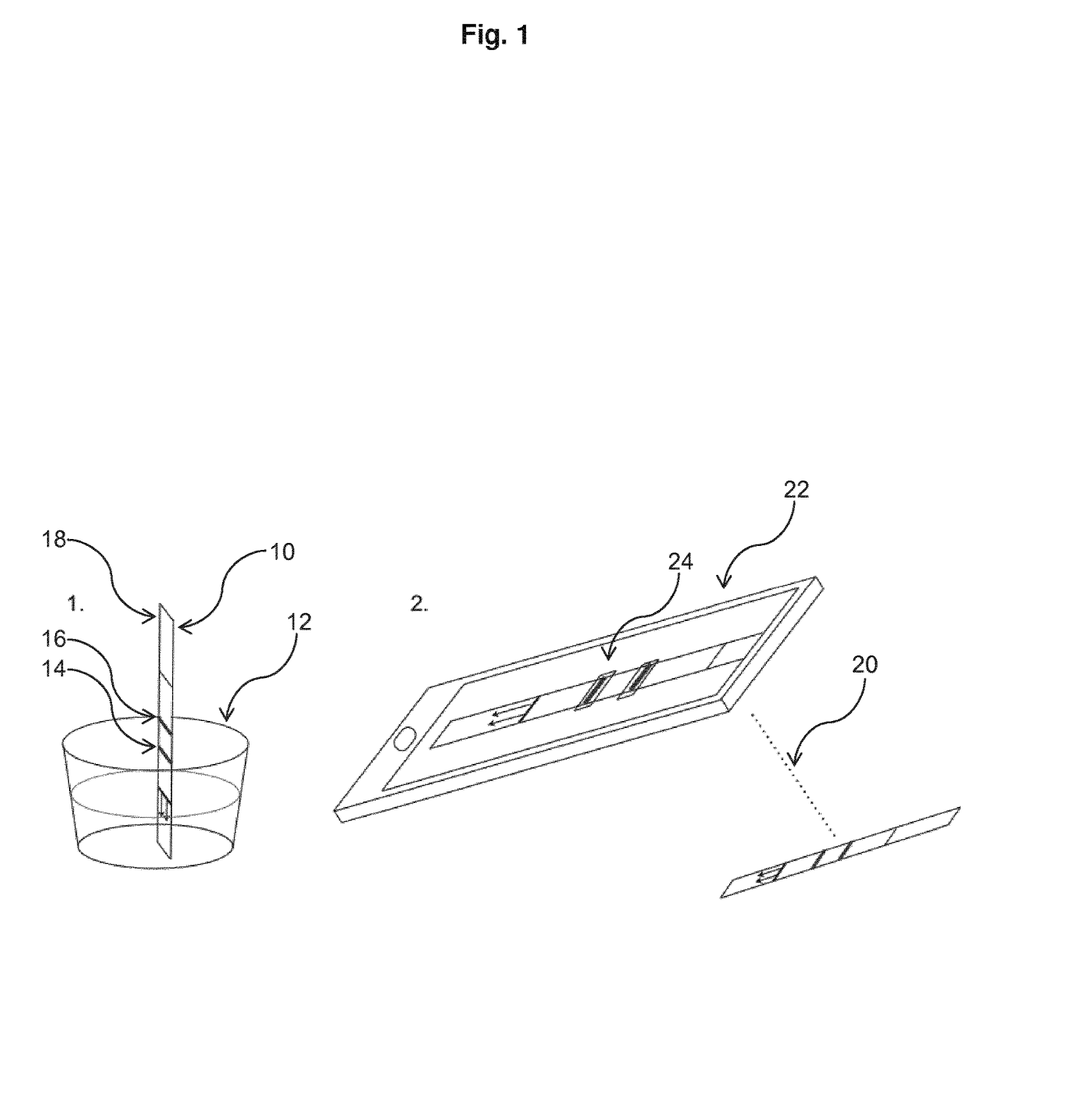
FIG. 1, shows an illustration of a test strip being exposed to urine and an exemplary device for estimation of an ovulation date with a test strip.

In the first part of FIG. 1, a FSH test strip 10 is shown onto which a urine sample is applied. A first end of the test strip 10 is soaked with urine in a cup 12 for around 5 seconds. After that, the test strip 10 is left to develop for up to 15 minutes. Subsequently, the test strip 10 is read by the device for estimation of the hormonal level for that given day. The test strip 10 comprises a detection zone 14, which indicates a FSH presence and concentration in the urine sample. The test strip 10 also comprises a control zone 16, into which the test sample permeates to indicate that the test strip 10 has been successfully prepared. The test strip 10 also comprises a blank zone 18 onto which no test sample is provided.

The full colour spectrum of the camera of the smartphone 22 is utilized to evaluate the FSH value of the test strip 10 with high accuracy, employing a suitable algorithm (such as disclosed in Ali K. Yetisen, J. L. Martinez-Hurtado, Angel Garcia-Melendrez, Fernando da Cruz Vasconcellos, Christopher R. Lowe. *A smartphone algorithm with inter-phone repeatability for the analysis of colourimetric tests. Sensors and Actuators B* 196 (2014) 156-160). The colour space representing the colour spectrum can vary. For example, it can be RGB, sRGB, LAB, HUV or any other. All of these spectra may be utilized with the smartphone 22 for estimation of an ovulation date according to the invention. First, the device is calibrated by exposing multiple test strips to multiple concentration values, and a concentration value is assigned to a corresponding colour subsequently.

After calibration, the colour of the detection zone exposed to unknown concentration urine sample 14 of the test strip 10 is determined and a FSH value is assigned to the test strip 10 depending upon the colour in the detection zone 14.

The device for estimation of an ovulation date is shown in the second part of FIG. 1. The device comprises a camera, which is provided at the device at the end of the dotted line 20. The device is configured as a smartphone 22. The smartphone 22 also comprises a processor (not shown) which is used to evaluate the colour data which is obtained by the camera. The smartphone 22 also comprises a display 24 for displaying the results of the ovulation estimation. The display 24 is also utilized to show the user the colour data of the test strip 10 and indicate whether or not correct colour data of the test strip 10 is obtained by the camera.

Multiple test strips 10 are provided and the FSH level is monitored over the period of multiple days by means of the smartphone 22.

For monitoring the FSH level, daily urine samples are applied to FSH test strips 10, starting shortly after menstruation. Colour data of each test strip 10 is obtained by the camera of the smartphone 22. For taking colour data of the test strip 10, the camera of the smartphone 22 is positioned a few centimeters and central over the test strip 10 and a picture of the test strip 10 is taken by the user or the colour data or the test strip 10 is processed by the smartphone 22 without the need of taking a distinctive picture.

In order to correct for different conditions such as different illumination etc., each colour data of the test strip 10 is subjected to a further calibration. For calibration, the colour of the blank zone 18 of the test strip, onto which no analyte is attached, is compared with the colour of the control zone 16 of the test strip, which has maximum colour change, induced by the urine sample. The first colour is set to denote a minimum FSH value, while the second colour is set to denote a maximum FSH value.

Starting from the first evaluation of the first test strip 10 shortly after menstruation, daily monitoring of the FSH value is conducted.

Figure 2:
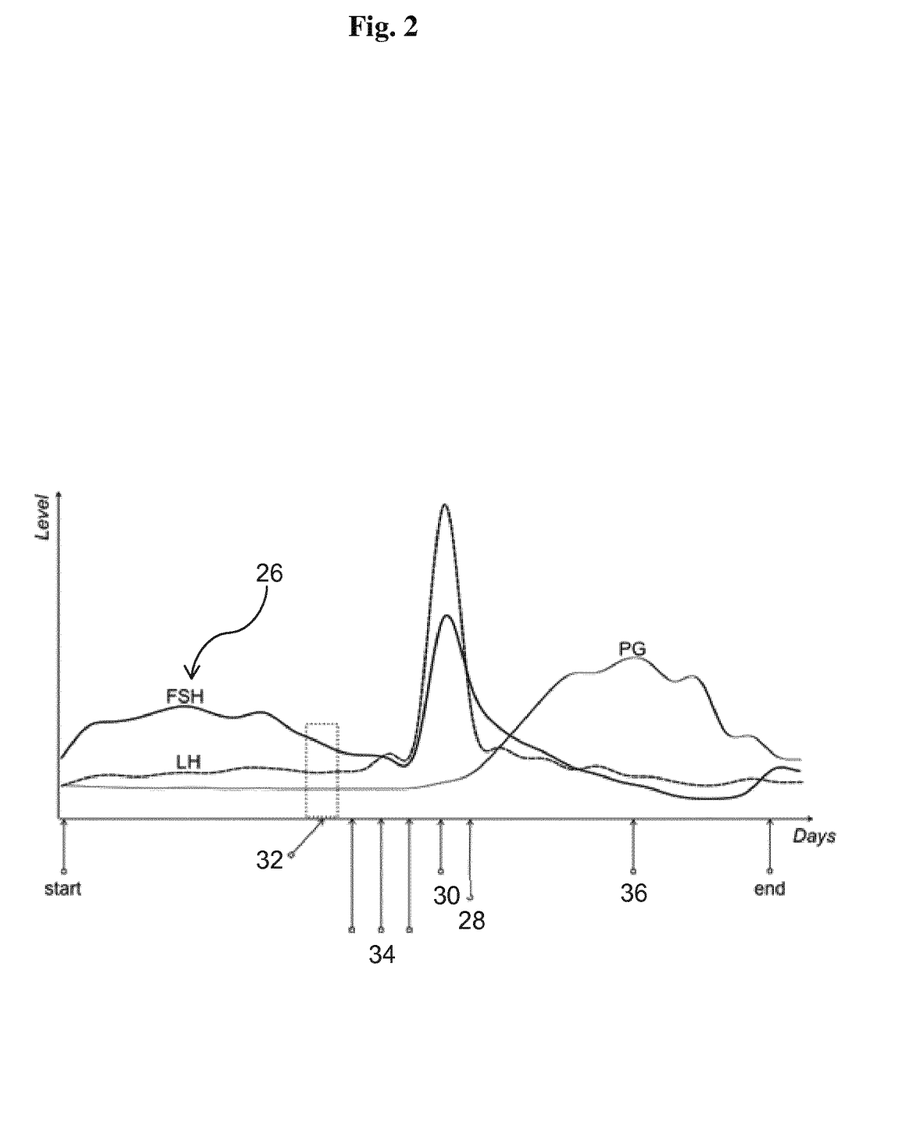
FIG. 2, shows exemplary levels of different female sex hormones throughout a menstruation cycle.

FIG. 2 shows the levels of FSH, LH, Oestrogen (E) and Progesterone (PG) over the course of a measurement cycle. As shown in FIG. 2, the FSH value reaches a first shallow peak 26 well before the LH value peaks 24 to 48 hours before ovulation. The first peak 26 of the FSH level occurs about 10 days before ovulation 28 and about 8 days before a second FSH peak 30, which occurs approximately about the same time as the LH peak 30. The measured values for FSH as depicted in FIG. 2 are typically 1 to 16 IU/L, for LH 3 to 74 IU/L and for Progesterone 0 to 20 IU/L.

Upon monitoring the FSH level by means of the device for estimation of an ovulation 28 (or ovulation date 28) as described with reference to FIG. 1, a first FSH downward trend is detected. In more detail, the first downward trend of FSH is characterized by a significant drop in the hormonal level of FSH over the course of multiple daily measurements. As can be seen in FIG. 2, the first shallow peak 26 of FSH is not a distinct and sharp peak as the LH/FSH peak 30. Rather, the first shallow peak 26 is characterized by a non-distinct hormonal plateau with successive ascending and descending FSH levels. The first downward trend is detected, if a significant descending FSH value is detected for the first time. In this regard, every measurement of an FSH value is measured within a certain measurement error of around 15% of the total hormonal level. Only if the descend is significant with respect to the measurement error, the first downward trend is detected. For example, measurements are taken over 6 subsequent days and the first downward trend is detected if the FSH value decreases significantly with respect to the value variation of the preceding measurements. The physiological range for 5% to 95% of the population is within 5 to 10 IU/L for the first shallow peak of FSH and within 2 to 6 IU/L for the lowest level of FSH. A significant drop in the hormonal level may be detected in successive measurements if the drop exceeds 0.7 to 8 IU/L, preferably 1 IU/L. Alternatively, a drop in the hormonal level may be detected if the drop exceeds 7% to 80%, preferable 10%, of the first shallow peak. The device detects the downward trend based on the concentration of FSH of multiple successive measurements.

The time when the first downward trend is detected is labeled as a detection window and denoted by the reference numeral 32. The detection window 32 is followed by the most fertile days 34 in the fertile window. In this regard, once a first downward trend of the FSH level is detected in subsequent test strips, the processor will determine that the FSH peak 26 has just occurred. Following this detection of the first FSH downward trend, the processor will output a corresponding signal and the display 24 will show an estimated ovulation date 28 to the user. Typically, this allows estimating the ovulation date 28 around five to seven days in advance of the actual ovulation date 28.

To enhance the accuracy of the device for estimation of an ovulation date 28, LH test strips are also used to monitor the LH level in subsequent urine samples. The monitoring of the LH level is conducted in the same way as the monitoring of the FSH level as described above. Once a significant rise in the LH level before the LH peak 30 is determined by the processor, an upcoming ovulation date 28 may be affirmed, and a respective result displayed to the user. Once the LH peak 30 is determined, the ovulation 28 can be confirmed, and a respective result displayed to the user through the display 24 of the smartphone 22. Also the second FSH peak 30, occurring approximately at the same time as the LH peak 30, may be detected by the processor and utilized to confirm an impending ovulation date 28.

In order to ensure that an ovulation 28 has occurred, the progesterone level may be monitored in a way as described above with respect to the monitoring of FSH and LH levels. The progesterone level—as can be seen in FIG. 2—peaks at peak 36 some days after the ovulation 28 has occurred. By monitoring the progesterone level, an ovulation 28 can be further confirmed when the progesterone level reaches a certain amplitude or follows an upward trend or a peak and a negative confirmation can be displayed on the display 24 of the smartphone 22, if the progesterone level does not reach a certain amplitude after the estimated ovulation date 28 or does not show an upward trend or a peak.

Figure 3:
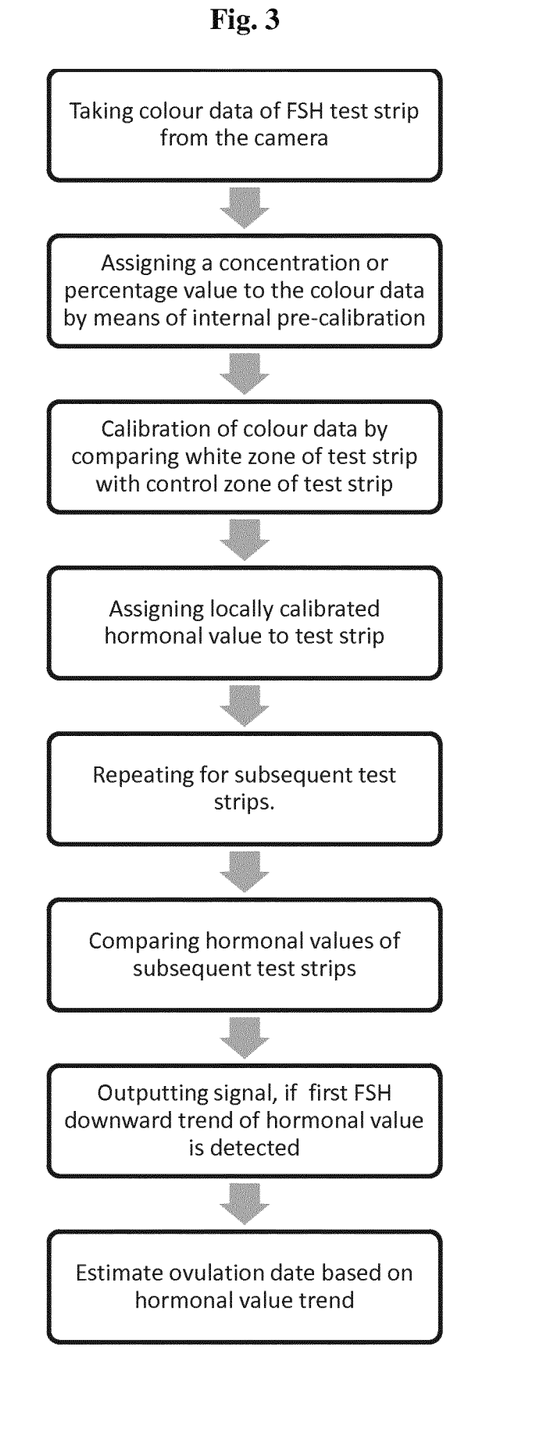
FIG. 3, shows an exemplary block diagram, illustrating the operation of the device for estimation of an ovulation date.

The subsequent steps as described above and which are performed by the method for estimation of an ovulation date are depicted in FIG. 3.

Figure 4:
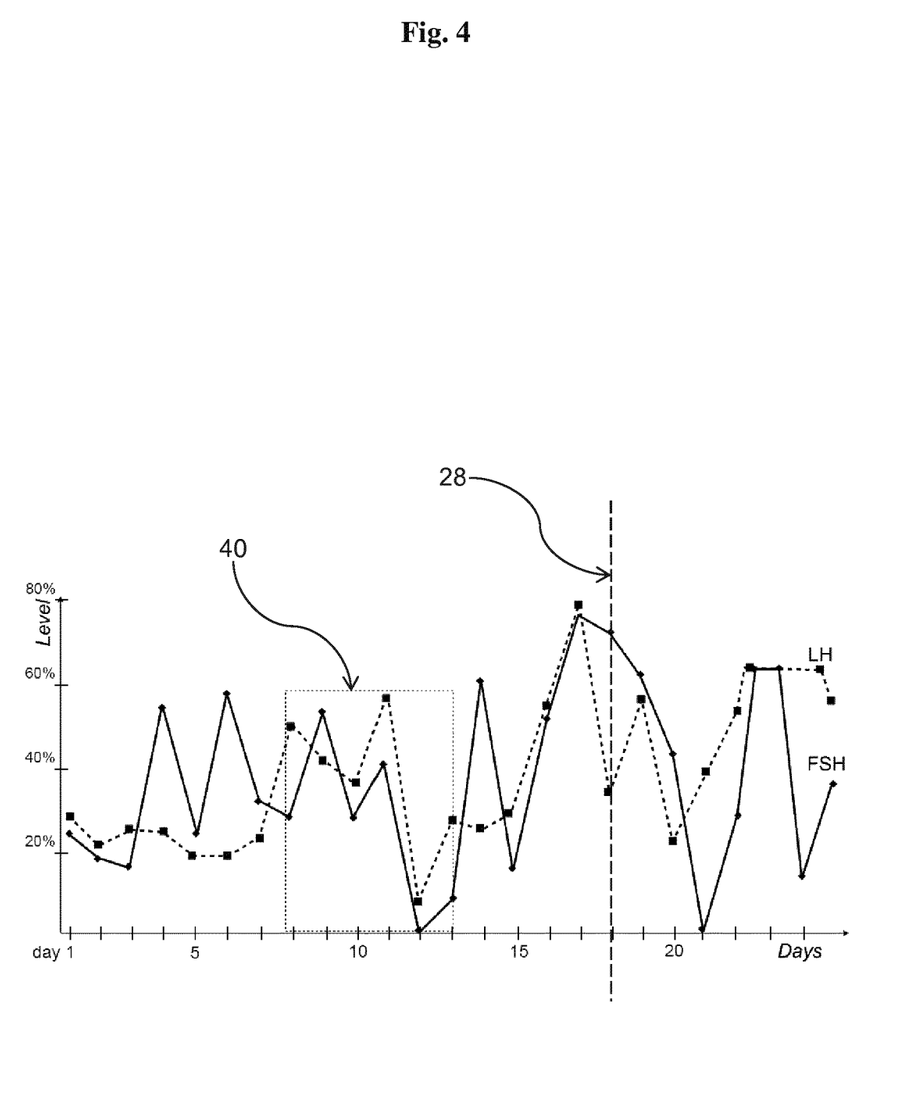
FIG. 4, shows an example hormonal profile.
Figure 5:
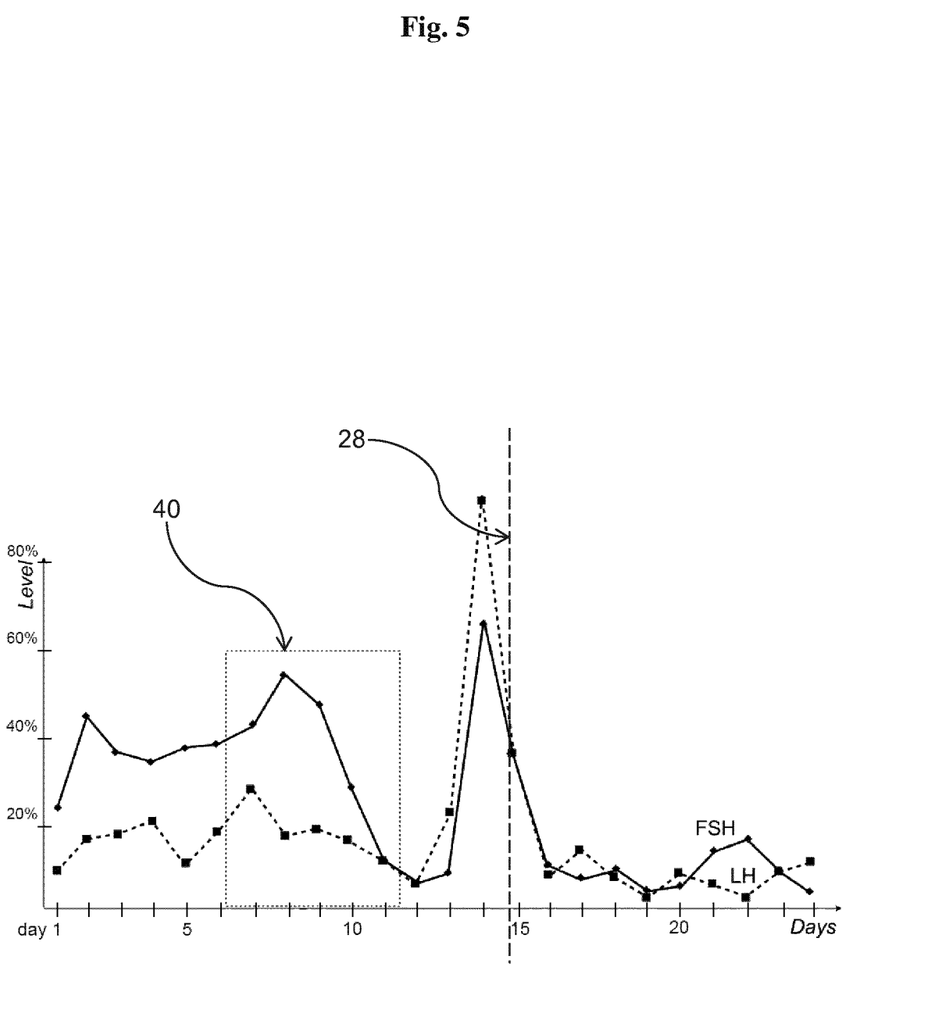
FIG. 5, shows a further example hormonal profile.
Figure 6:
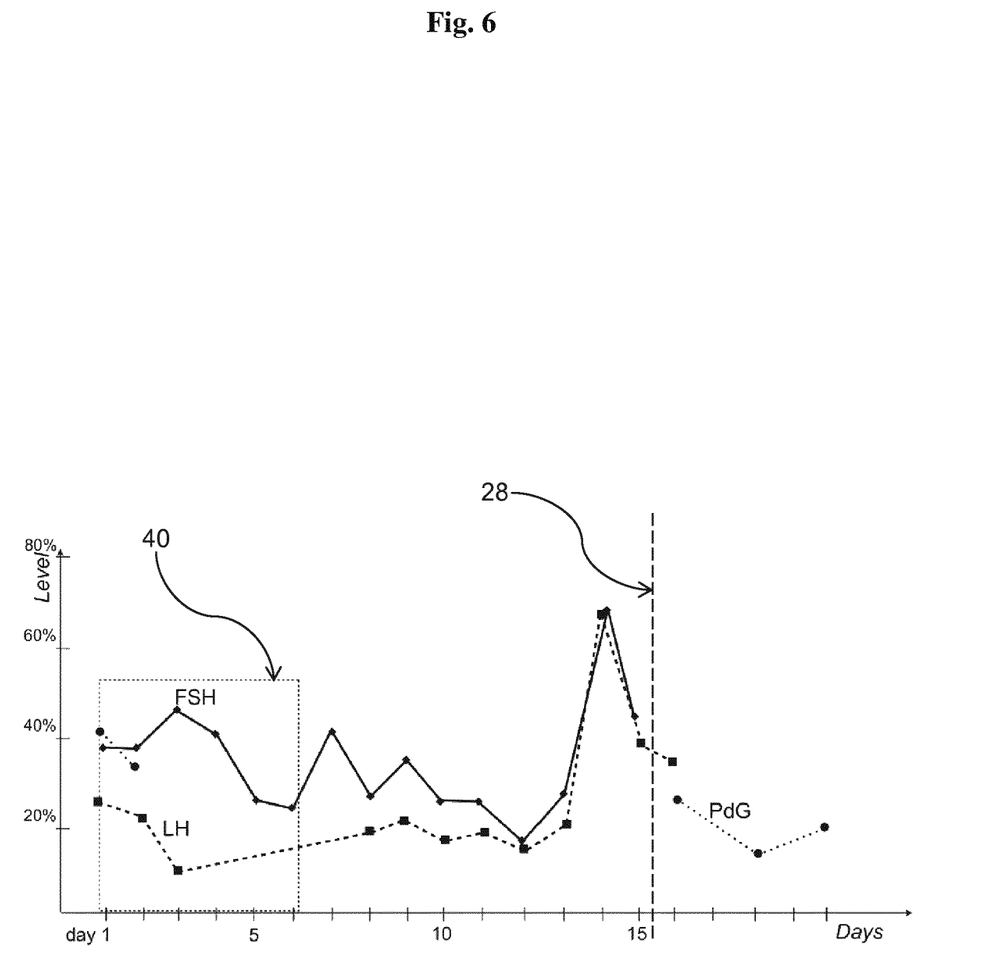
FIG. 6, shows a further example hormonal profile, in which PG is used as a further hormone.

In the following, example hormonal FSH profiles depicted in FIGS. 4 to 6 are discussed. The axis labeling in FIGS. 4 to 6 are days from the start of the menstruation on the abscissa. On the ordinate, concentration values of the respective hormones are denoted by a percentage value. The percentage value of the ordinate is the percentage value of the hormones on the test zones after a local calibration is performed by comparing the mapped concentration values of the control zone and blank zones, and normalizing them to the maximum and minimum range, thus accounting for light and strip quality variability, and enhancing the precision of the measurement. As can be seen from the example profiles, the first downward trend is not obvious to the human eye for a single profile in isolation. Therefore, an estimation is required using the above mentioned mathematical methods to find the first downward trend of FSH. Furthermore, confirming ovulation based on detecting hormonal peaks is also not obvious for the human eye for hormonal values obtained in urine. Particularly, a set of six values of consecutive measurements is analyzed. In this regard, the slopes of linear regressions of the six values, of the first five values and of the last five values within the set of six values are determined. Furthermore, the correlation coefficients of the three linear regressions are compared. The respective set of six measurement, which have led to a determination of a first FSH downward trend are indicated by reference numeral 40 in FIGS. 4 to 6 and the respective calculation results of the processor for the example hormonal profiles are presented below in tables 1 to 3.

FIG. 4 shows an example hormonal profile. In this profile, relative example hormonal values are reported by the device. In this case the hormonal level is reported as percentage change for daily measurements of first morning urine. In this example an FSH level is maintained high for a few days and it starts a relatively sharp decrease from day 9 from the first recorded point. In this example, a downward trend of FSH is less obvious, and the peaks of FSH and LH are less obvious, too. A first FSH downward trend 40 is identified at day 13 corresponding to the 13th measured point. According to a prediction model the ovulation date 28 can be estimated close to day 18, with highest chances six days after the first FSH downward trend at day 19. This is corroborated by a peak in LH observed at day 17. The first FSH downward trend is determined on basis of the calculation results of the processor in table 1.

TABLE 1

| Days | Slope 1 | Slope 2 | Slope 3 | CC 1 | CC 2 |
|---|---|---|---|---|---|
| 1-6 | 6.459868493 | 8.840542013 | 3.645439024 | 0.685 | 0.37 |
| 2-7 | 4.784929083 | 3.576474007 | 8.840542013 | 0.307 | 0.69 |
| 3-8 | 0.739106021 | -4.49225851 | 3.576474007 | -0.453 | 0.31 |
| 4-9 | -0.594184411 | 2.772085589 | -4.49225851 | 0.285 | -0.45 |
| 5-10 | 0.043045529 | -3.848672213 | 2.772085589 | -0.42 | 0.28 |
| 6-11 | -2.08502613 | 1.737581284 | -3.848672213 | 0.258 | -0.42 |
| 7-12 | -4.049069745 | -6.584313583 | 1.737581284 | -0.54 | 0.26 |
| 8-13 | -6.801177026 | -11.54994006 | -6.584313583 | -0.846 | -0.54 |

In table 1, "Slope 1" denotes the slope of the linear regression of the six values of consecutive measurements. "Slope 2" denotes the slope of the linear regression of the subset of the first five values within the set of six measurements. "Slope 3" denotes the slope of the linear regression of the subset of the last five values within the set of six measurements. "CC 1" denotes the first correlation coefficient of the linear regression of the first five values of the six measurements. "CC 2" denotes the second correlation coefficient of the linear regression of the last five values and the six measurements. As can be seen in table 1, on day 13, Slope 1, Slope 2 and Slope 3 are all negative for the last analyzed set of six values for days 8 to 13. Additionally, the respective correlation coefficients CC 1 and CC 2 are also negative. Hence, at day 13, the ovulation day 28 can be estimated to occur around day 18. This example shows that there is a very good correlation between the prediction and the actual ovulation date. This example is representative for the majority of menstruation cycles.

FIG. 5 shows a further example of a hormonal profile. In this example, the downward trend 40 of FSH is more obvious, however its beginning is not. The device for identification of a downward trend 40 of FSH outputs a signal at day 11 from the start of the measurements yielding an estimation of the ovulation date 28 at around day 17. An LH peak is detected at day 14 with an ovulation 28 confirmed after day 14. The LH peak corrects the predicted ovulation probability estimation. The first FSH downward trend is determined on basis of the calculation results of the processor in table 2.

TABLE 2

| Days | Slope 1 | Slope 2 | Slope 3 | CC 1 | CC 2 |
|---|---|---|---|---|---|
| 1-6 | 1.497580559 | -1.100609058 | 1.750393064 | -0.45 | 0.36 |
| 2-7 | -0.013807932 | 1.634595717 | -1.100609058 | 0.833 | -0.45 |
| 3-8 | 3.211203353 | 4.462609333 | 1.634595717 | 0.926 | 0.83 |
| 4-9 | 3.381887884 | 3.47392041 | 4.462609333 | 0.817 | 0.93 |
| 5-10 | -0.250330915 | -1.630016333 | 3.47392041 | -0.269 | 0.82 |
| 6-11 | -5.307976632 | -8.779014211 | -1.630016333 | -0.821 | -0.27 |

As can be seen in table 2, on day 11, Slope 1, Slope 2, Slope 3, CC 1 and CC 2 are all negative. Hence, at day 11, the ovulation day 28 can be estimated to occur at day 17, which is then corrected to occur at day 15 by the monitoring of the changes in the LH level.

FIG. 6 shows a further example hormonal profile. In this example, in addition to FSH and LH hormonal relative values, PG is also used. PG is measured on days 1 and 2 and then later on days 16, 18 and 21 after the ovulation 28 is confirmed by the LH peak from day 14. In this case the first FSH downward trend 40 is detected on day 6 from the start of the measurements and an ovulation 28 predicted around day 12. This estimation is again based upon the probability distribution of the ovulation data in dependence of the first FSH downward trend. This probability distribution has a maximum at six days after the first FSH downward trend. The ovulation 28 is confirmed by the LH peak at day 14, which is indicative of the actual ovulation to occur at day 15 and further corroborated by a decreasing PG signal. PG test strips in this case are a competitive assay for which decreasing detected values means an increase in concentration values, characteristic of an upward trend. PG values after ovulation 28 are compared also to PG values before ovulation 28. In this case there is a gap of LH values from day 4 to 7 which are not crucial for the prediction of ovulation 28. Also there are FSH and LH values missing after day 14 and 16 respectively. Similarly, PG values are missing from day 3 up to day 15. This shows that only the values necessary to make the prediction and identifying the trends are required.

The first FSH downward trend is determined on basis of the calculation results of the processor in table 3.

TABLE 3

| Days | Slope 1 | Slope 2 | Slope 3 | CC 1 | CC 2 |
|---|---|---|---|---|---|
| 1-6 | −3.63 | −5.61 | −2.22 | −0.77 | −0.40 |

As can be seen in table 3, on day 6, Slope 1, Slope 2, Slope 3, CC 1 and CC 2 are all negative. Hence, at day 6, the ovulation day 28 can be estimated to occur around day 12, with a confirmation by means of the LH peak at day 14. Hence, in this example, the ovulation date 28 is later than the estimated date. In such a case, the monitoring of the LH values is beneficial to confirm the specific date of ovulation. In a further example, the LH values may be checked simultaneously together with the FSH downward trend to increase accuracy, for example by analyzing whether simultaneous LH values before the measurement are on a baseline, a raise, or a peak, or a downward trend.

The last example does not show a good correlation between the prediction and the actual ovulation date. Such measurement series are observed only in exceptional cases, and the accuracy of the ovulation date estimation may be increased for future menstruation cycles by taking into account a series of menstruation cycles of a woman.

The exemplary embodiments described above illustrate but are not limiting. In view of the above discussed exemplary embodiments, other embodiments consistent with the above exemplary embodiments are now apparent to one of ordinary skill in the art.

The invention claimed is:

1. A device for reading and interpreting follicle-stimulating hormone (FSH) test strips for the estimation of an ovulation date, comprising:
   a camera, configured to obtain colour data of successive FSH test strips; and
   a processor, configured to evaluate the colour data obtained by the camera,
   wherein the processor is configured to determine a concentration value of each successive FSH test strip based on the colour data of the camera and to output a signal, if the processor determines that a first FSH downward trend of the FSH test strip values is occurring in the successive FSH test strips;
   wherein the first downward trend of FSH is determined by taking into account six test strip measurements of six consecutive days;
   wherein the processor is configured to determine an estimation of ovulation based on the first downward trend;
   wherein the processor is further configured to determine the slope of the linear regression of the six concentration values and to determine the slope of the linear regression of the first five concentration values and the slope of the linear regression of the last five values within the set of six concentration values;
   wherein the processor is further configured to compare the three slopes amongst themselves and wherein the processor is configured to determine a significant downward trend if the three slopes fall within a predetermined range.

2. A device for estimation of an ovulation date according to claim 1, wherein the colour data obtained by the camera encompasses multiple different wavelengths.

3. A device for estimation of an ovulation date according to claim 1, wherein the device further comprises a display, configured to display the estimation results of the device.

4. A device for estimation of an ovulation date according to claim 1, wherein the test strips each comprises one or more control zones, and wherein the processor is configured to calibrate the device based on the obtained camera data of the control zones.

5. A device for estimation of an ovulation date according to claim 1, wherein the test strips each comprises a blank zone, and wherein the processor is configured to calibrate the device based on the obtained camera data of the blank zone.

6. A device for estimation of an ovulation date according to claim 1, wherein the test strips each comprises one or more detection zones, and wherein the processor is configured to determine a concentration or percentage change value of the analyte on the detection zone based on the reading and evaluation of a change in colouration of the detection zone.

7. A device for estimation of an ovulation date according to claim 1, wherein the processor is configured to transform the test strip colour data from the camera into a percentage change or a numerical value change.

8. A device for estimation of an ovulation date according to claim 1, wherein the device is calibrated based upon at least one previous measurement of a test strip exposed to a standard concentration solution, or by a plurality of test strips exposed to different standard concentration solutions.

9. A device for estimation of an ovulation date according to claim 1, wherein the camera is configured to also obtain and the processor to evaluate colour data of luteinizing hormone (LH) test strips, estrogen test strips and/or progesterone test strips.

10. A device for estimation of an ovulation date according to claim 9, wherein the processor is configured to output a further second signal, if the processor determines that a rise or peak or downward trend of the LH value is occurring in successive LH test strips.

11. A device for estimation of an ovulation date according to claim 10, wherein the processor is configured to output a further third signal, if the processor determines that a rise or peak or trend of the progesterone value is occurring in successive progesterone test strips after the first downward trend of FSH value in the FSH test strips is determined, or rise or peak or downward trend of the LH value in the LH test strips is determined.

12. A device for estimation of an ovulation date according to claim 11, wherein the second signal is an affirmation signal and/or the third signal is a confirmation signal.

13. A device for estimation of an ovulation date according to claim 9, wherein the device is configured as a smartphone.

14. A device for estimation of an ovulation date according to claim 9, wherein the processor is configured to calibrate the device based upon at least one previous measurement cycle of the device.

15. A device for reading and interpreting FSH test strips for the estimation of an ovulation date, comprising:
   a camera, configured to obtain colour data of successive FSH test strips; and
   a processor, configured to evaluate the colour data obtained by the camera,
   wherein the processor is configured to determine a concentration value of each successive FSH test strip based on the colour data of the camera and to output a signal, if the processor determines that a first FSH downward trend of the FSH test strip values is occurring in the successive FSH test strips;

wherein the first downward trend of FSH is determined by taking into account FSH test strip values taken on consecutive days;

wherein the processor is further configured to determine three slopes of the linear regression of the FSH test strip values;

wherein the processor is further configured to compare the three slopes amongst themselves and wherein the processor is configured to determine the first downward trend if the three slopes fall within a predetermined range;

wherein the processor is configured to determine an estimation of ovulation based on the first downward trend;

wherein the first downward trend is determined when the three slopes are negative.

16. A device for reading and interpreting FSH test strips for the estimation of an ovulation date, comprising:

a camera, configured to obtain colour data of successive FSH test strips; and a processor, configured to evaluate the colour data obtained by the camera, wherein the processor is configured to determine a concentration value of each successive FSH test strip based on the colour data of the camera and to output a signal, if the processor determines that a first FSH downward trend of the FSH test strip values is occurring in the successive FSH test strips;

wherein the processor is configured to determine an estimated ovulation date at least 5 days in advance of the actual ovulation date based on consecutive test strip measurements taken on consecutive days between first and second FSH value peaks.

* * * * *